_United States Patent_ [19]

Sanford et al.

[11] 4,450,232

[45] May 22, 1984

[54] INCORPORATION OF PYRIDOXAL PHOSPHATE IN DRY ANALYTICAL ELEMENTS FOR THE DETERMINATION OF ENZYMES

[75] Inventors: Karl J. Sanford; John W. Sutherland; Jon N. Eikenberry, all of Rochester, N.Y.

[73] Assignee: Eastman Kodak Company, Rochester, N.Y.

[21] Appl. No.: 345,844

[22] Filed: Feb. 4, 1982

[51] Int. Cl.$^3$ .................... C12Q 1/00; C12Q 1/26; C12Q 1/52; C12Q 1/48
[52] U.S. Cl. .................................... 435/15; 435/4; 435/16; 435/25; 435/26; 435/805; 422/56; 422/57
[58] Field of Search ................. 422/56, 57; 435/4, 15, 435/16, 25, 26, 805

[56] References Cited

U.S. PATENT DOCUMENTS

| | | | |
|---|---|---|---|
| 3,992,158 | 11/1976 | Przybylowicz et al. | 422/57 |
| 4,066,403 | 5/1980 | Bruschi | 422/57 |
| 4,235,962 | 11/1980 | Sanderson | 435/16 |
| 4,241,179 | 12/1980 | Madappally et al. | 435/16 |
| 4,242,446 | 12/1980 | Madappally et al. | 435/26 |
| 4,255,384 | 3/1981 | Kitajima et al. | 422/56 |
| 4,318,982 | 3/1982 | Hornby et al. | 435/7 |

OTHER PUBLICATIONS

Bergmeyer et al., _Clinical Chemistry_, vol. 23 (5), pp. 887–893 (1977).
"International Federation of Clinical Chemistry, Provisional Recommendations on IFCC Methods for the Measurement of Catalytic Concentrations of Enzymes," Part 2 IFCC Method for Aspartate Aminotransferase, _Clin. Chem._ vol. 23, p. 887, 1977.
Bruns et al., "Evaluation of the IFCC-Recommended Procedure for Serum Aspartate Aminotransferase as Modified for Use With the Centrifical Analyzer", _Clin. Chem._, vol. 27, p. 156 (1981).
Hafkenscheid et al. "Influence of Pyridoxal-5'-phosphate on the Determination of the Alanine Aminotransferase and Aspartate Aminotransferase of Commercial Test Sera", _J. Clin. Chem. Clin. Biochem._, vol. 17, pp. 219–223 (1979).
Soo-se Chen et al, "Modification of Pig M$_4$ Lactate Dehydrogenase by Pyridoxal 5'-Phosphate", _Biochem J._, vol. 149, pp. 107–113 (1975).
"Reversable Modification of Pig Heart Mitochondrial Malate Dehydrogenase by Pyridoxal 5'-Phosphate", _Biochem. J._, vol. 151, pp. 297–303 (1975).
_Research Disclosure_, vol. 146, Jun. 1976, Item 14636.

_Primary Examiner_—Thomas G. Wiseman
_Assistant Examiner_—Deborah A. Grossman
_Attorney, Agent, or Firm_—J. Lanny Tucker

[57] ABSTRACT

Enzymes which are activated by pyridoxal phosphate are assayed in a dry analytical element which includes a high coverage of pyridoxal phosphate. The coverage of pyridoxal phosphate is such that the multiplication product of the coverage and the spreading coefficient of the element results in a reagent mixture concentration of at least about 0.9 mmole per liter when a liquid sample is contacted with the element thereby eliminating the need for a preincubation of the sample with a solution containing pyridoxal phosphate. The reactions for the determination of the enzymes are initiated by contact of the dry elements with a liquid sample.

9 Claims, 1 Drawing Figure

INCORPORATION OF PYRIDOXAL PHOSPHATE IN DRY ANALYTICAL ELEMENTS FOR THE DETERMINATION OF ENZYMES

FIELD OF THE INVENTION

The present invention relates to dry analytical elements which are useful in determining the amount of pyridoxal phosphate activated enzyme in a liquid sample. The elements of the present invention are particularly useful in quantitating aspartate aminotransferase and alanine aminotransferase enzymes.

Description Relative to the Prior Art

Transaminase enzymes are enzymes which catalyze the transfer of an α-amino group from an α-amino acid to an α-keto acid. These enzymes are also sometimes referred to as aminotransferases. Two of the most clinically significant aminotransferase enzymes are L-alanine:α-ketoglutarate aminotransferase, EC 2.6.1.2 (commonly referred to as alanine aminotransferase or ALT) and L-aspartate:α-ketoglutarate aminotransferase, EC 2.6.1.1 (commonly referred to as aspartate aminotransferase or AST) (including mitochondrial and cytoplasmic isoenzymes).

Both of these enzymes are clinically significant in that they are found in high concentration in either the heart muscle or the liver. Thus, their elevated presence in serum is an indication of a recent myocardial infarction or liver disease.

ALT and AST are similar in that they both contain a prosthetic group. The prosthetic group is pyridoxal phosphate which must be present for the enzyme to be active. The pyridoxal phosphate forms a Schiff base with a lysine group in the active site of the enzyme. In the transaminase reaction, the α-amino group of the substrate displaces the amine portion of the lysine group of the active site of the enzyme forming a transient Schiff base with pyridoxal phosphate. The pyridoxal phosphate then transfers the α-amino group to the α-keto acid and recombines with the lysine of the enzyme. Pyridoxal phosphate is also the prosthetic group or activator for a number of other enzymes.

Pyridoxal phosphate is a derivative of pyridoxine (Vitamin $B_6$). It is also sometimes referred to as pyridoxal-5'-phosphate, phosphopyridoxal, P-5-P, PLP or PDP. Pyridoxal phosphate has a molecular weight of about 265.

While serum generally contains a certain amount of endogenous pyridoxal phosphate, in analyses for ALT and AST, as well as other enzymes having this prothetic group, it is desirable to supplement the serum amounts of pyridoxal phosphate by preincubating a sample to be analyzed for AST or ALT with a solution containing additional pyridoxal phosphate. Thus, any enzyme which might be in the apo form, or inactive form, is activated by this preincubation step. While the need for pyridoxal phosphate preincubation in the ALT and AST assay was debated in the literature for several years, preincubation is now accepted as being necessary in order to bring out all of the potential enzyme activity which is in a sample. Thus, the International Federation of Clinical Chemistry recommends a 10 minute incubation of a sample in a solution which contains 0.1 mmole per liter of pyridoxal phosphate (see "International Federation of Clinical Chemistry, Provisional Recommendations on IFCC Methods for the Measurement of Catalytic Concentrations of Enzymes", "Part 2 IFCC Method for Aspartate Aminotransferase", *Clin Chem* 23,887 (1977)).

The need for a preincubation step in this standard IFCC method has been an impediment to the adoption of this method in automatic analyzers. Many automatic analyzers are adapted to accommodate this preincubation step only with great difficulty. Thus, there has been a great incentive to eliminate, if possible, preincubation of the sample with pyridoxal phosphate solution. The ultimate goal is to develop an assay which is sample initiated. That is, an assay wherein all the reagents, including pyridoxal phosphate, are together and the assay is performed by adding only the sample to the reaction mixture without the need for preincubation.

One example of an attempt to dispense with the preincubation step is illustrated in the article of Bruns et al, "Evaluation of the IFCC-Recommended Procedure for Serum Aspartate Aminotransferase as Modified for Use With the Centrifical Analyzer", *Clin. Chem.*, Vol. 27, page 156 (1981). While these authors were able to adapt a conventional solution automatic analyzer to the IFCC method by substantially reducing the preincubation period, their data does show that there is a significant advantage with even a short random preincubation time. In other words, they found that eliminating the preincubation time entirely produced an inferior assay.

Because of the importance of pyridoxal phosphate on the activation of the apo-enzyme form of AST and ALT, this activation has been widely studied. For example, it is known that in dilute solution, activation of the apo-enzyme occurs at low concentrations of pyridoxal phosphate. Thus, the IFCC recommends that the incubation be carried out in a 0.1 mmole per liter pyridoxal phosphate solution. Other studies have indicated that somewhat higher levels of pyridoxal phosphate might be desirable, for example, up to 0.3 mmole per liter. However, in solution, additional pyridoxal phosphate gave little, if any, further activation. In addition, because of the spectral absorption of pyridoxal phosphate and the possible inhibition of the coupling enzyme used in the indicator reaction of the assay, higher concentrations of pyridoxal phosphate are not used in solution assays (see Hafkenscheid et al, "Influence of Pyridoxal-5'-phosphate on the Determination of the Alanine Aminotransferase and Aspartate Aminotransferase of Commercial Test Sera", *J. Clin. Chem. Clin. Biochem.*, Vol. 17, pp. 219–223, (1979); Soo-se Chen et al, "Modification of Pig $M_4$ Lactate Dehydrogenase by Pyridoxal 5'-Phosphate", *Biochem J.*, Vol. 149, pp. 107–113, (1975) and "Reversable Modification of Pig Heart Mitochondrial Malate Dehydrogenase by Pyridoxal 5'-Phosphate", *Biochem. J.*, Vol. 151, pp. 297–303 (1975)).

Dry analytical elements which are an improvement over conventional solution methods have been recently developed. In a typical dry analytical element, the reagents which are needed for the assay of a particular analyte are coated in a layer which is then dried. The sample, such as serum, is then contacted with the dried element, the reaction takes place and the results are detected.

It is possible to adapt dry analytical elements for the determination of enzyme concentrations in samples. For example, U.S. Pat. No. 3,992,158 to Przybylowicz and Millikan discloses a useful element for the determination of AST. Such an element would be useful; however, in order to comply with the requirements of the IFCC method, the serum would have to be first preincubated with a solution containing pyridoxal phosphate for 10 minutes. Even though a shorter time might be used, Bruns et al clearly show that an assay having no preincubation is inferior to one having even a short random incubation. The methods which are designed to use the dry analytical element of Przybylowicz and Millikan most preferably use undiluted samples. In order to provide preincubation time, it would be necessary to treat samples for the determination of the transaminases with a solution containing pyridoxal phosphate before placing them in the analyzer. It is readily apparent that this is undesirable.

A detailed description of dry analytical elements for the determination of transaminase enzymes is found in *Research Disclosure*, Vol. 146, June 1976, Item 14636. No mention is made of pyridoxal phosphate in this publication. *Research Disclosure is a publication of Industrial Opportunities Ltd.; Homewell, Havant; Hampshire, PO9 1EF, United Kingdom*.

A dry analytical element for the determination of transaminase enzymes without a preincubation step would be desirable. Such an element should provide a sensitive and accurate assay which provides a degree of activation which is comparable to the IFCC solution method (which includes a 10 minute pre-incubation step).

SUMMARY OF THE INVENTION

We have found that it is highly desirable to include an extremely large quantity of pyridoxal phosphate in a dry analytical element for the determination of enzymes which are activated by pyridoxal phosphate. The coverage and spreading characteristics are such that the reaction mixture which results when the liquid sample is contacted with the element has a pyridoxal phosphate concentration of greater than about 0.9 mmole per liter. The amount of pyridoxal phosphate which is useful in the elements of the present invention is far in excess of what would be expected to be useful from dilute solution studies. While most solution methods use 0.1 mmole per liter in the preincubation mixture, and while it is known that high levels of pyridoxal phosphate cause absorption and possible coupling enzyme deactivation, the amount of pyridoxal phosphate in the elements of the present invention is more than three times that which is known to be the upper limit in solution methods. Unexpectedly, it has been found that the incorporation of this large quantity of pyridoxal phosphate produces a dry element which is useful in an assay which does not require preincubation of the sample prior to contact with the remainder of the reagents. Thus, the elements of the present invention are useful with samples which have had a minimum of preanalysis preparation, such as undiluted serum samples.

In use, the amount of a given reagent in the reaction mixture in a dry analytical element is related to both the coverage of that reagent on the dry analytical element and the spreading characteristics of the sample on the element. For a given coverage of reagent, the amount of reagent in a given volume of reaction mixture depends on the area which that given volume of solution occupies on the element. For the purposes of the present invention it has been found desirable to describe the spreading characteristics of a dry analytical element in terms of a spreading coefficient. While a dry analytical element does not have a reaction mixture concentration until contacted with liquid sample, the concentration which would result is determined by multiplying the coverage (e.g., in mmoles per $m^2$) by the spreading coefficient (e.g., in $m^2$ per liter). The spreading coefficient is the area occupied per unit volume of sample applied to the element. The spreading coefficient for any particular element is an inherent characteristic and is easily determined by contacting a sample of the element with a known volume of liquid, measuring the area over which the liquid spreads and then calculating the spreading coefficient by dividing the area by the volume of liquid. More specific examples and conditions for this measurement are given later in the specification.

Thus, in one aspect of the present invention there is provided a dry analytical element for the determination of an analyte in a sample wherein said analyte is an enzyme which is activated by pyridoxal phosphate, said element comprising a support having thereon a layer comprising reagents capable of producing a detectable change in response to the presence of the activated form of said enzyme wherein said element contains a layer comprising pyridoxal phosphate at a coverage such that the multiplication product of said coverage and the spreading coefficient of the element results in a reaction mixture concentration of pyridoxal phosphate of greater than about 0.9 mmole per liter.

DETAILED DESCRIPTION OF THE INVENTION

Figure 1:
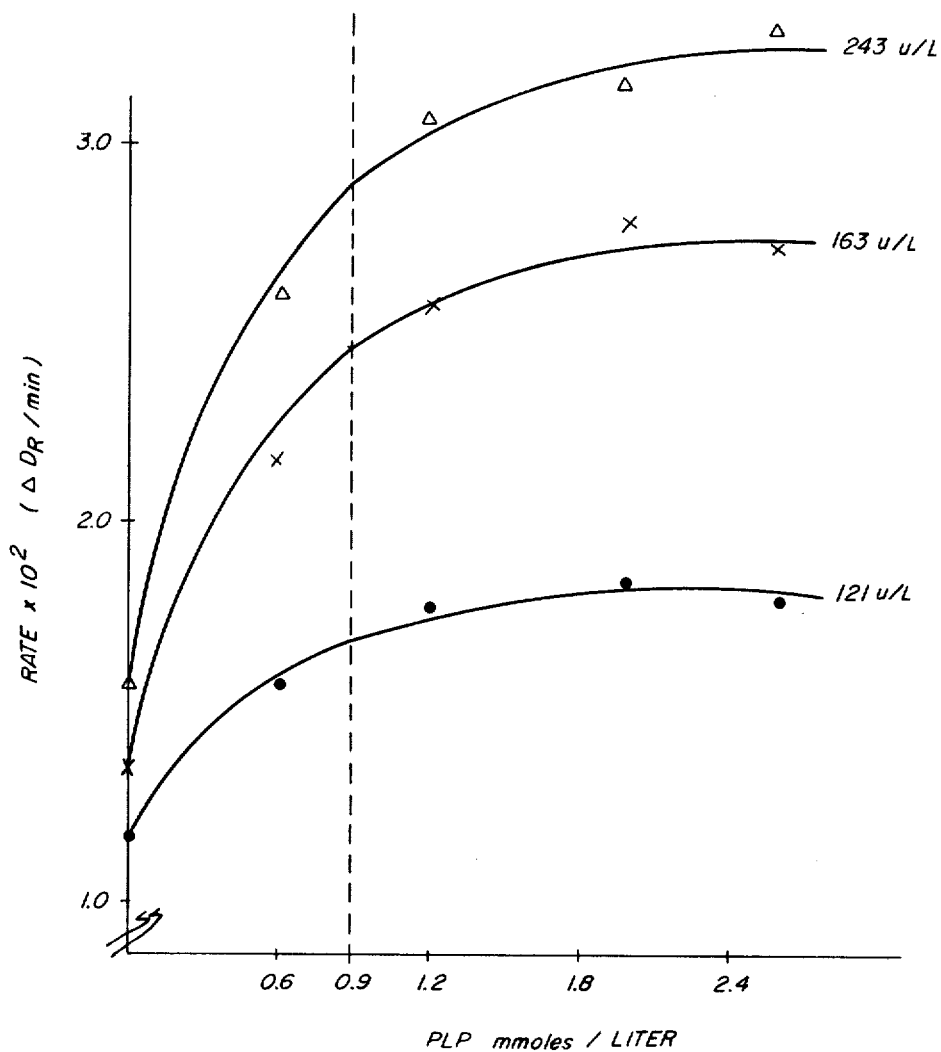
FIG. 1 is a plot of the response of a dry analytical element for the determination of AST as a function of the coverage of pyridoxal phosphate on the element for a series of calibrator solutions. The calibrator solutions contain only the apo-form of the enzyme and thus the plot illustrates the relationship between the degree of activation of the enzyme and the coverage of the pyridoxal phosphate.

The present invention is described in relation to dry analytical elements for the determination of AST and ALT. It will be understood, however, that other enzymes which are activated by pyridoxal phosphate are quantitated by elements containing a high level of this activator. By choice of suitable detecting reagents, enzymes such as other transaminases, for example glutamate-cysteine transaminase, and other transaminases described in table 16-4 on page 684 of Mahler et al, *Biological Chemistry*, Harper and Row, 1966; isomerases, for example isomers for analine, glutamate, proline, lysine and serine and dicarboxylases, for example those described in Mahler et al, cited above, at page 685, are determined.

The elements of the present invention include a high coverage of pyridoxal phosphate, i.e., in excess of that coverage which would produce a 0.9 mmole per liter concentration. We have found that the relationship between activation and pyridoxal phosphate concentration in a dry analytical element using undiluted serum is dramatically different from solution activation. While the general shapes of the activation curves are similar, in solution a plateau region is reached at very low levels of pyridoxal phosphate. For example, Hafkenschield et al (article cited above) found that the activation curve was substantially flat after about 0.2–0.3 mmoles per liter in a solution study. We have found that for a dry analytical element using undiluted serum the curve does not begin to flatten out until about a concentration of 0.9 mmole per liter—about three times the maximum solution value (see Example 2 and FIG. 1) is reached.

In particularly preferred embodiments, the elements contain sufficient pyridoxal phosphate to produce a reaction mixture concentration of at least about 2.0 mmoles per liter. Between about 0.9 and 2.0 mmoles per liter, there is some continuing improvement in the degree of activation. At levels higher than about 2.0 mmoles per liter, little further improvement is seen. Levels higher than 2.0 mmoles per liter are not detrimental to the performance of the element but the cost of pyridoxal phosphate places a practical limit on the amount incorporated. It is preferred to use a slight excess above 2.0 mmoles per liter to insure complete activation. The exact amount depends on the particular enzyme being activated. For ALT the optimum is near 2 mmoles per liter. For AST the optimum is near 3 mmoles per liter.

The pyridoxal phosphate is included in the element by a variety of methods. For example, the pyridoxal phosphate is simply dissolved in the coating composition for the desired layer. Alternatively, a dispersion of a high boiling liquid having the pyridoxal phosphate dissolved therein is included in the coating composition. In yet another alternative, the pyridoxal phosphate is associated with an amino containing polymer such as albumin which in turn is included in the coating composition.

Pyridoxal phosphate is particularly useful in the assay of AST. The preferred reagent composition which is capable of producing a detectable change in response to the presence of activated AST include NADH, L-aspartate, α-ketoglutarate and malate dehydrogenase (MDH). AST catalyzes the reaction of L-aspartate and α-ketoglutarate to oxalacetate and L-glutamate. In the next step, the oxalacetate and NADH react in the presence of the malate dehydrogenase to produce malate and NAD. The amount of AST in the sample is related to the rate of disappearance of NADH. Many samples, for example, blood serum, often contain endogenous pyruvate which would interfere with the malate dehydrogenase catalyzed reaction. In order to substantially eliminate the interference from pyruvate, the reagent composition for the determination of AST frequently contains lactate dehydrogenase (LDH). Alternatively oxamate is included to reduce pyruvate interference. Immediately after the sample is mixed with the reagent composition, the lactate dehydrogenase catalyses the rapid consumption of the pyruvate. Subsequently, the rate of NADH disappearance is monitored and is substantially free from the effects of pyruvate.

ALT is another enzyme which uses the activator pyridoxal phosphate. A preferred detecting reagent composition for the determination of ALT includes NADH, L-alanine, α-ketoglutarate and lactate dehydrogenase. In a manner similar to the assay for AST, any ALT in a sample catalyzes the reaction of L-alanine and α-ketoglutarate to L-glutamate and pyruvate. The pyruvate and NADH react in the presence of the lactate dehydrogenase to produce lactate and NAD. Again, the rate of disappearance of NADH is monitored and is related to the amount of ALT in the sample.

While the described NADH based methods for ALT and AST are currently preferred, dry analytical elements which contain other reagents capable of producing a detectable change in the presence of the activated form of these enzymes are also improved by the incorporation of high levels of pyridoxal phosphate. For example NAD to NADH indicator reactions are useful. Useful reagents are described, for example, in Henry R. J., *Clinical Chemistry: Principles and Technics*, Harper & Row, New York, N.Y., Second Ed., 1974, pp 873–893. Useful reagents including pyruvate oxidase are described in U.S. Pat. No. 4,246,342. Useful reagents including glutamate dehydrogenase are described in Ger. Pat. No. 2,431,779. Other useful reagents include citrate synthase/DTNB and are described in *Anal. Biochem.*, 35, pp. 405–410 (1970).

The transaminase dry analytical elements of the present invention preferably include, in addition to the high coverage of pyridoxal phosphate, a high coverage of NAD or NADH. Preferably, the coverage of NAD or NADH is such that the multiplication product of the coverage and the spreading coefficient is sufficient to provide an NAD or NADH concentration in the reaction mixture of between about 1 mmole per liter and 8 mmoles per liter. The high level of NADH provides for improvements in dynamic range and linearity of response of a dry analytical element for the determination of a transaminase.

Useful dry analytical elements according to the present invention are made by simply coating the reagent composition which includes the detecting reagents, pyridoxal phosphate and any other reagents, such as a buffer, onto a suitable support. In alternative embodiments, the support is coated with a number of layers, some of which contain one or more reagents. In particularly preferred embodiments, a multilayer element is formed which includes a spreading layer to improve spreading of the sample on the element. Optionally, the spreading layer contains one or more reagents of the detecting reagent composition. Useful spreading layers include layers made from fibrous materials such as paper or fabric.

The layer containing the detecting reagents must be in fluid communication with the pyridoxal phosphate reagent. This means that all the reagents are in the same layer with pyridoxal phosphate or are in separate layers which are adjacent or separated from each other by interlayers; all the layers being permeable to the sample, solubilized reagents and reaction products.

Particularly useful dry analytical elements are those which comprise a support having thereon an isotropically porous, nonfibrous spreading layer and, interposed between the support and the spreading layer a reagent layer. Isotropically porous, non-fibrous spreading layers are described in U.S. Pat. No. 3,992,158 to Przybylowicz and Millikan and U.S. Pat. No. 4,258,001 to Pierce et al. Compositions and methods for the formation of dry analytical elements are described in these patents.

Where possible, it is particularly desirable to include the substrates for the enzyme under analysis in the spreading layer of the dry analytical element. Since the enzymes are relatively large molecules, the location of the substrates for the enzymes in the porous spreading layer facilitates the contact of the enzyme in the sample with the substrates. As a result, the lag time, or the time required for the reaction to begin to take place, is reduced. Further, elements having the substrates in the spreading layer exhibit improved long term keeping.

While it is preferred to have the substrates in the spreading layer, it is preferred to have the pyridoxal phosphate in a separate reagent layer including a binder such as gelatin. By including the pyridoxal phosphate with a binder, the long term keeping of the element is improved.

The spreading coefficient for any particular element is determined by contacting the element with a known volume of sample. In calculating the spreading coefficient, the volume of sample should be chosen so that the element does not become saturated with fluid. After the element has been contacted with the known volume of sample, the area over which the sample spreads on the element is measured. To facilitate measurement of the area, the measurement of spreading coefficient is optionally made with a sample containing a dye so that the area is easily visible. The area produced by the sample divided by the volume of the sample is the spreading coefficient.

Within broad limits, the spreading coefficient for a particular element is substantially independent of the viscosity of the sample which is used to calculate the spreading coefficient. It is desirable to use the most viscous fluid in calculating the spreading coefficient. The currently preferred fluid for measuring the spreading coefficient is blood serum.

Also within broad limits, the spreading coefficient is substantially independent of the method of applying the sample to the element. In the currently preferred method, a stable pendant drop is dispensed from a container and the element is brought up to touch the drop onto the element. This method is more completely described in U.S. Pat. No. 4,041,995.

The spreading coefficient for a dry analytical element having the isotropically porous spreading layer described in the Przybylowicz and Millikan patent, cited above, was determined as follows: a 10 microliter drop of human serum was spotted on an element similar to the element of Example 1 of the Przybylowicz and Millikan patent except that the spreading layer contained barium sulfate and a cellulose acetate binder. The resulting spot had a diameter of about 0.8 cm. Thus, the area that was produced by the 10 microliter drop was 0.50 cm$^2$. Therefore, the spreading coefficient for this element is 0.050 cm$^2$ per microliter. In order to achieve a reaction mixture concentration of at least 0.9 mmole per liter, the coverage of pyridoxal phosphate on an element having these spreading characteristics would have to be at least about 0.05 g per m$^2$.

It is usually desirable to include a buffer in the reagent composition for the determination of enzymes. A wide variety of buffers are useful (see for example Good et al, "Hydrogen Ion Buffers for Biological Research", *Biochemistry*, Vol. 5, page 467 (Feb. 1966)). Particularly convenient buffers include N-tris(hydroxymethyl)methylamino ethane sulfonic acid (TES) and tris(hydroxymethyl)amino ethane (TRIS). Other useful buffers include imidazole, diethanolamine and triethanolamine.

Materials and elements which are adapted to use the described reagent composition including the detecting reagents and pyridoxal phosphate are described, for example, in U.S. Pat. Nos. 3,092,465, 3,418,099, 3,418,083, 2,893,843, 2,893,844, 2,912,309, 3,008,879, 3,802,842, 3,798,064, 3,298,739, 3,915,647, 3,917,453, 3,993,594, 3,936,357, 4,270,920, 4,248,829, 4,255,384, 4,256,693, U.K. Pat. No. 2,052,057 and *Research Disclosure*, Vol. 146, June 1976, Item 14638.

The following examples are presented.

EXAMPLE 1

Dry analytical elements for the determination of AST were prepared. The elements varied in the coverage of pyridoxal phosphate (PLP). Represented schematically, the elements had the structure:

Spreading Layer: barium sulfate, cellulose acetate binder, polyurethane, Triton X-405 ®, sodium α-ketoglutarate, sodium aspartate
Subbing Layer: poly(N—isopropyl acrylamide)
Reagent Layer: gelatin, Triton X-405 ®, buffer: N—tris(hydroxymethyl)methyl-2-aminoethane sulfonic acid (TES), NADH, MDH, LDH, pyridoxal phosphate various levels and gelatin hardener
Support: poly(ethylene terephthalate)

The polyurethane binder in the spreading layer promotes the cohesion of the spreading layer and is available from the B. F. Goodrich Co. under the name Estane ®. The subbing layer is present to promote the adhesion of the spreading layer to the reagent layer.

A 10 microliter sample of human serum was spotted on one of the elements described above. The sample was completely absorbed into the coated layers of the element and produced a spot having a diameter of 0.8 cm. The spreading coefficient for these elements was therefore 0.050 cm$^2$ per microliter.

Aliquots from forty-eight samples of hospital patient blood serum were assayed for AST activity by a modified IFCC reference method (37° C., 30 minutes pyridoxal phosphate incubation). This established an AST reference value for each patient sample.

Four aliquots (10 microliters each) from each patient sample were then spotted on four separate samples of each dry analytical element. The reflection density ($D_R$) of each element was monitored between 150–300 seconds after spotting.

A patient calibration line was established by regressing the activity for each patient sample (as determined by the reference assay) versus the individual rates measured experimentally on the described elements. Using this regression line the total error variance $\sigma_E$ (also referred to as Sy.x) was calculated and from the four replicates, the method precision $\sigma_o$ (also known as pooled precision) was calculated. Random bias $\sigma_e$ was also calculated from $\sigma_o$ and $\sigma_E$ (see Lawton et al, "Statistical Comparison of Multiple Analytic Procedures: Application to Clinical Chemistry", *Technometrics*, Vol. 21, No. 4, page 397 (1979)). Sensitivity is the reciprocal of the slope of the regression line. Table I summarizes the results.

TABLE I

| Example | PLP Level g/m$^2$ | mmole/liter | $\sigma_e$ | $\sigma_o$ | $\sigma_E$ | Sensitivity $\Delta D_R$/min/U/L |
|---|---|---|---|---|---|---|
| 1 | 0.05 | 0.95 | 11.1 | 4.6 | 12.0 | 5.67 × 10$^{-5}$ |
| 2 | 0.11 | 2.08 | 10.1 | 3.9 | 10.8 | 8.78 × 10$^{-5}$ |
| 3 | 0.16 | 3.03 | 9.3 | 3.2 | 9.8 | 8.80 × 10$^{-5}$ |

The data show that each element was capable of producing an excellent AST assay. The fact that the $\sigma_E$ for all elements is low indicates that substantially all of the apo-form of the enzyme in the serum has been converted to the active form. Otherwise, because of the varying ratio of active to inactive enzyme in serum samples one would expect higher variability in comparison with the standard assay which completely activates all enzyme by way of a 10 minute preincubation with pyridoxal phosphate. Further, increasing coverages of pyridoxal phosphate from 0.95 mmoles per liter to 2.08 mmoles per liter improved the $\sigma_E$ and sensitivity. Further increases in pyridoxal phosphate level showed lesser improvements in $\sigma_E$ and sensitivity.

EXAMPLE 2

This example illustrates the ability of the elements of the present invention to activate the apo-form of AST without the need for preincubation.

The ability of elements of the invention to activate the apo-form of the enzyme was tested by preparing samples which contained only the apo-form of AST and then measuring the response of elements with varying amounts of pyridoxal phosphate.

Dry analytical elements for the determination of AST were prepared and are represented schematically as follows:

---
Spreading Layer: Avicel ®, poly(vinylpyrrolidone), binder, α-ketoglutarate and L-aspartate
Reagent Layer: gelatin, buffer: imidazole, oxamate, NADH, pyridoxal phosphate various coverages
Support: poly(ethylene terephthalate)
---

Table II lists the coverages of pyridoxal phosphate in the various elements in this example.

TABLE II

| Experiment | Pyridoxal Phosphate | |
|---|---|---|
| | g/m$^2$ | mmoles/L |
| Comparative | 0 | 0 |
| Comparative | 0.02 | 0.6 |
| 4 | 0.04 | 1.2 |
| 5 | 0.064 | 1.9 |
| 6 | 0.086 | 2.5 |

Mitochondrial AST (mAST) was isolated from human liver using the procedure described in DiCola et al, *Acta. Vitamin Enzymol,* Vol. 30, page 28 (1976).

Cytoplasmic AST (cAST) was isolated from outdated red blood cells obtained from the Red Cross using the procedure described in *Clin Chem*, Vol. 18, page 374 (1972).

Preparation of the apo form of each isoenzyme was according to the following procedure:

A 15 U/mL solution of the isoenzyme was made 4 millimolar in aspartate. This solution was held at room temperature for 2 hours. Then, the solution was made 500 millimolar in sodium phosphate pH 6.0 and incubated overnight at 25° C. The solutions were then ultrafiltered and buffered to pH 7.8 with 10 millimolar TES.

Samples of mAST apoenzyme were spiked into human serum in which all AST activity had been eliminated and which was substantially free from endogenous pyridoxal phosphate. Solutions were prepared which contained 243, 163 and 121 U/L mAST.

Aliquots of each solution were spotted on samples of each element described above. The reflection density was monitored and for each solution-element pair a $\Delta D_R$ per minute was determined. FIG. 1 is a plot of $\Delta D_R$ per minute against pyridoxal phosphate concentration for each sample solution of mAST.

The data for the apo mitochondrial isoenzyme show the following:

(1) The enzyme in the solutions was substantially inactive. While some small activity was observed with the element containing no pyridoxal phosphate, this may have been due to some small amount of residual active AST caused by residual pyridoxal phosphate in the serum into which the enzyme was spiked.

(2) The apo enzyme was incompletely activated in this dry element format having no preincubation by 0.6 mmole per liter pyridoxal phosphate in the reaction mixture. This concentration represents double the maximum level which has been suggested for solution-type assays.

(3) The data show a plateau region for activation beginning at about 0.9 mmole per liter pyridoxal phosphate in the reaction mixture.

The data for the apo cytoplasmic isoenzyme were plotted in a similar manner. While the overall level of activation was lower for this isoenzyme, the same conclusions with respect to the activation by pyridoxal phosphate in the elements were made.

The invention has been described in detail with particular reference to preferred embodiments thereof, but it will be understood that variations and modifications can be effected within the spirit and scope of the invention.

What is claimed is:

1. A dry analytical element for the determination of an analyte in a liquid sample wherein said analyte is an enzyme activated by pyridoxal phosphate, said element comprising a support having thereon a layer comprising a reagent composition capable of producing a detectable change in response to the presence of the activated form of said enzyme wherein said element contains a layer comprising pyridoxal phosphate at a coverage such that the multiplication product of said coverage and the spreading coefficient of the element results in a substantially uniform reaction mixture concentration of pyridoxal phosphate of greater than about 0.9 mmole per liter.

2. A dry analytical element for the determination of an analyte in a liquid sample wherein said analyte is an enzyme which is activated by pyridoxal phosphate, said element comprising a support having thereon, in order, a reagent layer and a spreading layer wherein said layers comprise a reagent composition capable of producing a detectable change in response to the presence of the activated form of said enzyme and wherein at least one of said layers comprise pyridoxal phosphate at a coverage such that the multiplication product of said coverage and the spreading coefficient of the element results in a substantially uniform reaction mixture concentration of pyridoxal phosphate of greater than about 0.9 mmole per liter.

3. A dry analytical element for the determination of an analyte in a liquid sample wherein said analyte is an enzyme which is activated by pyridoxal phosphate, said element comprising a support having thereon, in order, a reagent layer and an isotropically porous spreading layer wherein said layers comprise a reagent composition capable of producing a detectable change in response to the presence of the activated form of said enzyme wherein said reagent layer comprises a binder and pyridoxal phosphate wherein the coverage of said pyridoxal phosphate is such that the multiplication product of said coverage and the spreading coefficient of the element results in a substantially uniform reaction mixture concentration of pyridoxal phosphate of greater than about 0.9 mmole per liter.

4. A dry analytical element according to claims 1, 2 or 3 wherein the spreading coefficient and pyridoxal phosphate coverage are such that the reaction mixture concentration of pyridoxal phosphate is greater than about 2.0 mmoles per liter.

5. A dry analytical element according to claim 1, 2 or 3 wherein said enzyme is aspartate aminotransferase and said detecting reagents comprise NADH, L-asparate, α-ketoglutarate and malate dehydrogenase.

6. A dry analytical element according to claim 1, 2 or 3 wherein said enzyme is aspartate aminotransferase and said detecting reagents comprise NADH, L-asparate, α-ketoglutarate, lactate dehydrogenase and malate dehydrogenase.

7. A dry analytical element according to claim 1, 2 or 3 wherein said enzyme is alanine aminotransferase and said reagents comprise NADH, L-alanine, α-ketoglutarate and lactate dehydrogenase.

8. A method for activating an enzyme in a liquid sample with pyridoxal phosphate, said method comprising the step of contacting said sample with a dry element comprising a support having thereon at least one layer comprising pyridoxal phosphate at a coverage such that the multiplication product of said coverage and the spreading coefficient of the element results in a substantially uniform reaction mixture concentration of pyridoxal phosphate is greater than about 0.9 mmole per liter.

9. A method for the determination of an analyte in a liquid sample wherein said analyte is an enzyme which is activated by pyridoxal phosphate said method comprising the steps of (a) contacting said sample with a dry analytical element comprising a support having thereon a layer comprising a reagent composition capable of producing a detectable change in response to the presence of the activated form of said enzyme said element containing at least one layer comprising pyridoxal phosphate at a coverage such that the multiplication product of said coverage and the spreading coefficient of the element results in a substantially uniform reaction mixture concentration of pyridoxal phosphate is greater than about 0.9 mmole per liter, and (b) determining the rate of said detectable change.

* * * * *